US007923994B2

(12) United States Patent
Hoyt

(10) Patent No.: US 7,923,994 B2
(45) Date of Patent: Apr. 12, 2011

(54) SPIRAL MAGNETIC FIELD APPARATUS AND METHOD FOR PIPELINE INSPECTION

(76) Inventor: Philip M. Hoyt, Murray, UT (US)

( * ) Notice: Subject to any disclaimer, the term of this patent is extended or adjusted under 35 U.S.C. 154(b) by 0 days.

(21) Appl. No.: 12/615,912

(22) Filed: Nov. 10, 2009

(65) Prior Publication Data

US 2010/0117635 A1 May 13, 2010

Related U.S. Application Data

(60) Provisional application No. 61/113,692, filed on Nov. 12, 2008.

(51) Int. Cl.
*G01R 33/12* (2006.01)
(52) U.S. Cl. ........................................ 324/220
(58) Field of Classification Search .................... 324/220
See application file for complete search history.

(56) References Cited

U.S. PATENT DOCUMENTS

| 3,786,684 | A | 1/1974 | Wiers et al. |
| 4,100,809 | A | 7/1978 | Bobrov et al. |
| 4,127,035 | A | 11/1978 | Vasile |
| 4,295,214 | A | 10/1981 | Thompson |
| 4,691,572 | A | 9/1987 | van den Berg et al. |
| 5,085,082 | A | 2/1992 | Cantor et al. |
| 5,454,276 | A | 10/1995 | Wernicke |
| 5,537,876 | A | 7/1996 | Davidson et al. |
| 5,565,633 | A | 10/1996 | Wernicke |
| 6,065,348 | A | 5/2000 | Burnett |
| 7,548,059 | B2 | 6/2009 | Thompson et al. |
| 2009/0078048 | A1 | 3/2009 | Alers et al. |

OTHER PUBLICATIONS

Beuker, Thomas et al., "SCC Detection Improvement Using High Resolution EMAT Technology," International Pipeline Pigging, Integrity Asssessment and Repair Conference, Houston, TX, Feb. 5-6, 2004.
Shevaldykin, V.G. et al., "EMA Transformation in Pulsed Magnetic Field and its Use in Portable Instruments for Acoustic Measurements," 16th World Conference on NDT, Montreal, Canada, Aug. 30-Sep. 3, 2004.
Aron, Jeff et al., "Development of an EMAT In-Line Inspection System for Detection, Discrimination, and Grading of Stress Corrosion Cracking in Pipelines," U.S. Department of Energy Award No. DE-FC26-01NT41154, Feb. 2005.
Klann, Martin et al., "Pipeline Inspection with the High Resolution EMAT ILI-Tool: Report on Field Experience," Proceedings of IPC 2006 6th International Pipeline Conference, Calgary, Alberta, Canada, Sep. 25-29, 2006.
Beuker, Thomas et al., "In-line Inspection with High Resolution EMAT Technology Crack Detection and Coating Disbondment," International Pipeline Pigging, Integrity Assessment and Repair Conference, Houston, TX, Feb. 12-13, 2008.

*Primary Examiner* — Reena Aurora
(74) *Attorney, Agent, or Firm* — Warren M. Pate, LLC

(57) ABSTRACT

A system and method are disclosed for inspecting the wall of a pipeline while traveling therethrough. The system may comprise a portion of pipe comprising a pipe wall forming a cylindrical tube defining a circumferential direction and an axial direction. The system may further include an in-line inspection tool positioned within the portion of pipe. The in-line inspection tool may include a frame extending in the axial direction and at least one magnet connected to the frame and positioned to generate a magnetic field. The magnetic field may be orientated obliquely with respect to the circumferential and axial directions of the pipeline. The inspection tool may include a transmitter connected to the frame to generate an inspection signal within the magnetic field.

20 Claims, 10 Drawing Sheets

SPIRAL MAGNETIC FIELD APPARATUS AND METHOD FOR PIPELINE INSPECTION

RELATED APPLICATIONS

This application claims the benefit of U.S. Provisional Patent Application Ser. No. 61/113,692 filed Nov. 12, 2008, which is hereby incorporated by reference.

BACKGROUND

1. Field of the Invention

This invention relates to pipeline inspection tools, and more particularly to apparatus and methods for data collection on an in-line inspection tool.

2. Background of the Invention

Oil, petroleum products, natural gas, hazardous liquids, water, and the like are often transported using pipelines. The majority of these pipelines are constructed from steel pipe. Once installed, a pipeline will inevitably corrode or otherwise degrade. Proper pipeline management requires identification, monitoring, and repair of defects and vulnerabilities of the pipeline. For example, information collected about the condition of a pipeline may be used to determine safe operating pressures, facilitate repair, schedule replacement, and the like.

Typical defects of a pipeline may include corrosion, gouges, dents, cracks, and the like. Corrosion may cause pitting, general wall loss, or cracking, thereby lowering the maximum operating pressure of the pipeline. Vulnerabilities may also include combined stress and chemical or biological action such as stress corrosion cracking. Without detection and preemptive action, all such defects and vulnerabilities may lead to pipeline failure.

Information on the condition of a pipeline is often collected using an in-line inspection (ILI) tool. Ferromagnetic pipelines can be inspected for defects, including cracks extending along the axis of a pipe, by a limited number of technologies. These technologies include magnetic flux leakage (MFL) inspection, ultrasonic (UT) inspection, eddy current inspection, and, in certain applications, inspection using electromagnetic acoustic transducers (EMATs).

EMAT inspection has failed to gain widespread use on in-line inspection tools. This failure has largely been the result of an inability to separate meaningful signal from the surrounding noise. Moreover, problems have arisen from the complex geometries involved. For example, building on the disclosures of Bobrov et al. (U.S. Pat. No. 4,100,809), Alers et al. (U.S. Publication No. 20090078048) disclose a device that projects a transverse shear, ultrasonic, guided wave, that wave is oriented at an angle of ten degrees to sixty degrees from the axis of the pipeline. However, when the wave strikes an axially oriented defect (e.g., an axially oriented crack), it does so at an oblique angle and is, consequently, reflected away from the transmitter at a mirror image angle. Thus, the proper location for a corresponding receiver cannot be determined with specificity, as it depends on the location of the defect with respect to the transmitter.

While some technologies are more adversely affected by the foregoing factors than are others, all such techniques may be improved with better signal detection, recognition, and geometries. What is needed is a better device and method for the generation and reception of pulsed signals for the various inspection technologies.

SUMMARY

In contrast to conventional in-line inspection tools and to the device disclosed and advocated by Alers et al., selected embodiments in accordance with the present invention may include a magnetic field oriented obliquely with respect to both the axial and circumferential directions of the pipeline being inspected. While this oblique magnetic field may be described herein primarily in the context of EMAT technology, it is not limited in application to that technology. An oblique magnetic field in accordance with the present invention may be applied to other defect detection technologies, including magnetic flux leakage inspection.

In selected embodiments, a system in accordance with the present invention may include an EMAT traveling on an in-line inspection tool proximate an interior surface of a pipeline. The EMAT may generate a circumferentially directed, transverse shear wave in the wall of the pipeline. The wave may be guided in a circumferential direction around the pipeline between the interior and exterior surfaces of the pipe wall.

In certain embodiments, an EMAT may comprise a meander coil oriented with its long axis parallel to the axial direction of the pipeline. One or more magnets may generate a magnetic field about the coil. The magnetic field generated by the one or more magnets may be oriented with respect to the circumferential direction of the pipeline at an angle between zero degrees and ninety degrees.

When the angle between the circumferential direction of the pipeline and the magnetic field is between zero degrees and ninety degrees, and the long axis of the meander coil is parallel to the axial direction of the pipeline, only a circumferential, transverse, shear wave may be transmitted. The amplitude of the circumferential, transverse, shear wave may be increased when the magnetic field is oriented with respect to the circumferential direction of the pipe at an angle between ten and sixty degrees.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION

Figure 1:
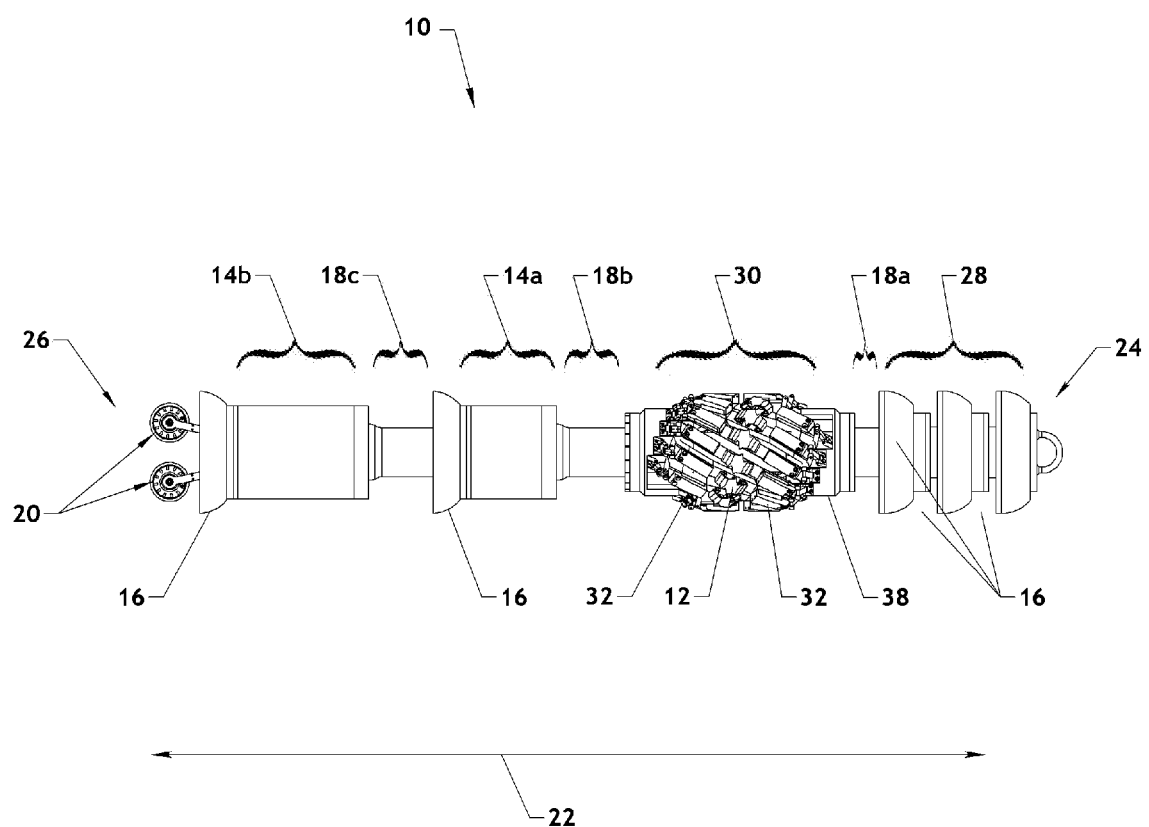
FIG. 1 is an elevation view of one embodiment of an in-line inspection tool in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention as claimed, but is merely representative of various embodiments of the invention. The illustrated embodiments of the invention will be best understood by reference to the drawings, wherein like parts are designated by like numerals throughout.

Referring to FIG. 1, an in-line inspection tool 10 or vehicle 10 in accordance with the present invention may comprise various components including one or more inspection assemblies 12, canisters 14, driving cups 16, couplers 18, position sensors 20, and the like. Depending on the configuration of the in-line inspection tool 10 and the size of the pipeline to be inspected, the arrangement and number of components (e.g., the number of canisters 14) may vary.

Canisters 14 may house equipment such as one or more processors, memory devices, and batteries. The driving cups 16 may center the tool 10 within the pipeline and enable fluid traveling within a pipeline to engage the tool 10, thereby pushing the tool 10 through the pipeline. In selected embodiments, driving cups 16 may be formed of a somewhat flexible polyurethane or similar material. Couplers 18 may support bending of the tool 10, enabling the tool 10 to accommodate bends in the pipeline. Like the driving cups 16, in selected embodiments the couplers 18 may be formed of somewhat flexible polyurethane or similar material. Alternatively, couplers 18 may comprise a mechanical pivoting device.

An in-line inspection tool 10 may extend in a longitudinal direction 22 from a head end 24 to a tail end 26. The various components 12, 14, 16, 18, 20 of an in-line inspection tool 10 may be arranged in series. For example, in the illustrated embodiment, the head end 24 of a tool 10 may comprise a head section 28 comprising one or more driving cups 16. Following the head section 28 may be a primary sensor suite 30. A coupler 18a may extend to connect the head section 28 to the primary sensor suite 30.

In selected embodiments, an in-line inspection tool 10 in accordance with the present invention may include one or more inspection assemblies 12 connected to an interior structure 38 (e.g., interior cylinder 38). Each inspection assembly 12 may include one or more magnets 32, signal sources, sensors, or combinations thereof positioned so as to travel along the interior of a pipe wall being inspected. Such signal sources and sensors may generate and receive a wide variety of signals oriented in any of many directions. While certain embodiments of the present invention may be discussed or illustrated in the context of an in-line inspection tool using EMAT technologies generating magnetostrictive stress waves, it should be understood that the concepts of the present invention are not limited to EMAT technologies. Concepts in accordance with the present invention (e.g., an oblique magnetic field) may be applied to other defect detection technologies, including magnetic flux leakage inspection, ultrasonic inspection, and eddy current inspection.

Following the primary sensor suite 30 may be a first canister 14a. In one embodiment, the first canister 14a may house the hardware providing the processing and memory devices for the in-line inspection tool 10. A coupler 18b may extend to connect the primary sensor suite 30 to the first canister 14a.

The first canister 14a may be followed by another driving cup 16. A coupler 18c may engage a first canister 14a and extend rearward to engage a second canister 14b. In one embodiment, the second canister 14b may house batteries providing the power for the in-line inspection tool 10. In selected embodiments, a driving cup 16 may connect to the second canister 14b. One or more position sensors 20 may then engage the second canister 14b, driving cup 16, or some combination thereof to form the tail end 26 of the in-line inspection tool 10. In one embodiment, the position sensors 20 may comprise one or more odometers 20 positioned to roll along the interior surface of the pipeline and measure the distance traveled by the in-line inspection tool 10.

Figure 2:
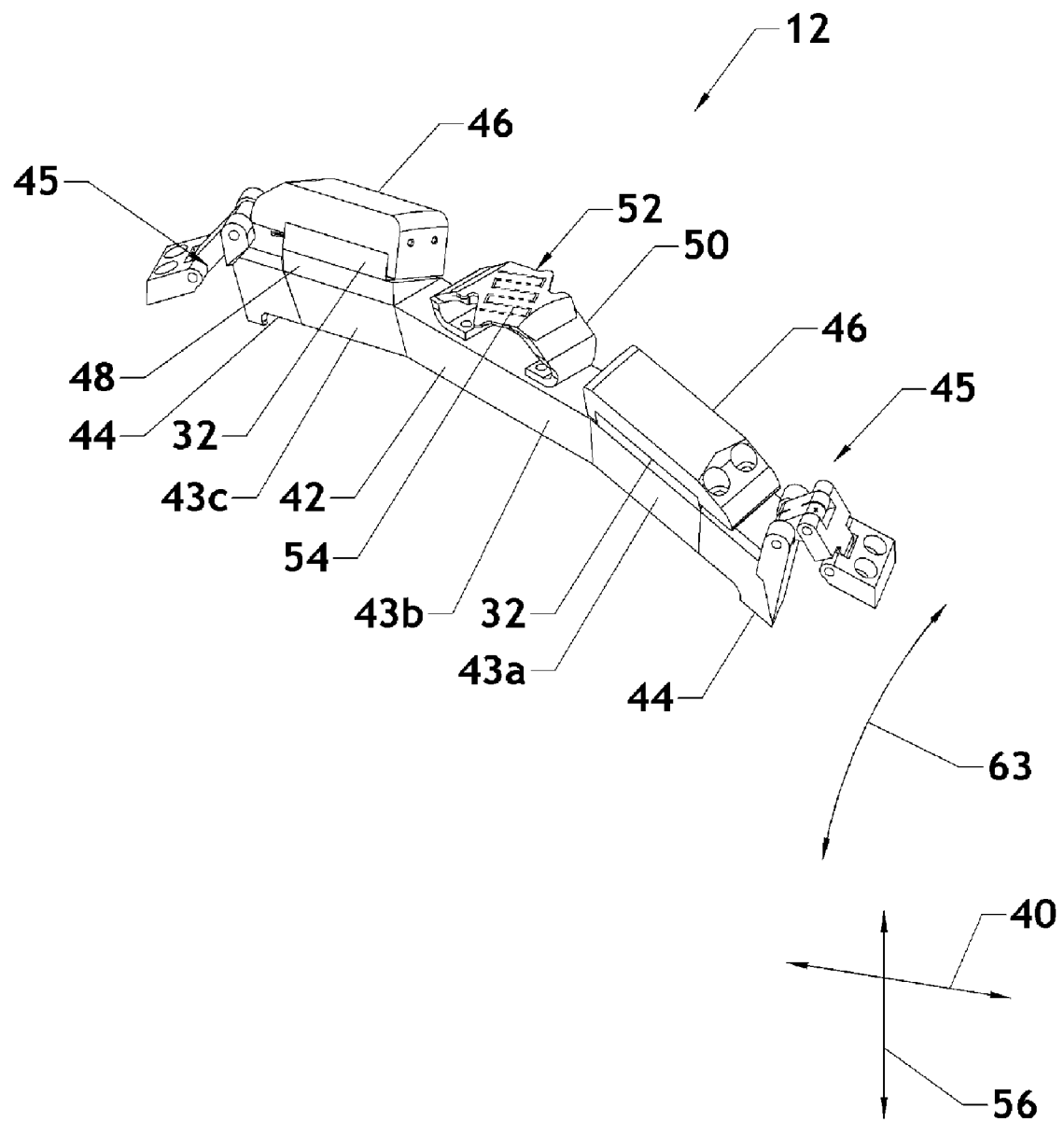
FIG. 2 is a perspective view of one embodiment of an inspection assembly comprising an EMAT inspection device and linkages in accordance with the present invention.

Referring to FIG. 2, in selected embodiments, a primary sensor suite 30 may include inspection assemblies 12 having linkages, linkage movement, sensor housings, inter-sensor-housing movement, etc. disclosed in U.S. patent application Ser. No. 12/478,137 filed Jun. 4, 2009 and U.S. patent application Ser. No. 12/403,754 filed Mar. 13, 2009, both of which are hereby incorporated by reference. Similarly, embodiments in accordance with the present invention may utilize the pseudorandom binary sequence apparatus and method disclosed in U.S. patent application Ser. No. 12/538,104 filed Aug. 7, 2009, which is hereby incorporated by reference.

In certain embodiments, a primary sensor suite 30 may include inspection assemblies 12 distributed circumferentially (i.e., in a circumferential direction 63) about a central axis 40 of an in-line inspection tool 10. Each inspection assembly 12 may include a backbar 42 (e.g., armature 42) for supporting the various components of the inspection assembly 12. A linkage mount 44 may be positioned at each end of a backbar 42. Linkages 45 may engage an inspection assembly 12 via the linkage mounts 44 and extend therefrom to connect the inspection assembly 12 to an interior cylinder 38 forming the back bone of the primary sensor suite 30. Accordingly, inspection assemblies 12 may partially or fully encircle the interior cylinder.

In selected embodiments utilizing EMAT inspection, a backbar 42 may support one or more magnets 32. In certain embodiments, an inspection assembly 12 may include a magnet mount 46 providing an interface between a backbar 42 and a magnet 32. The magnet mount 46 may protect the magnet 32. The magnet mount 46 may also assist in transferring flux into the wall of the pipe being inspected.

In selected embodiments, a backbar 42 may support two magnets 32, one magnet 32 proximate each end thereof. For selected inspection assemblies 12, a sensor mount 50 may secure to the backbar 42 at a location between the two magnets 32. The sensor mount 50 may connect a sensor housing 52 to the backbar 42.

A backbar 42 in accordance with the present invention may extend obliquely with respect to the central axis 40 of an in-line inspection tool 10. Accordingly, to closely track the interior surface of the pipeline being inspected and to avoid unwanted interference with an underlying structure (e.g., cylinder) of the in-line inspection tool 10, a backbar 42 may have an arced shape or configuration.

In selected embodiments, the arc formed by a backbar 42 may be smooth and continuous. In other embodiments, the arc formed by a backbar 42 may comprise multiple straight segments. For example, as shown in the illustrated embodiment, a backbar 42 may comprise a first straight segment 43*a* proximate one end, a second straight segment 43*b* proximate the middle of the backbar 42, and a third straight segment 43*c* proximate the other end.

In certain embodiments, in addition to an arced shape, a backbar 42 may include other features facilitating close tracking of the interior surface of the pipeline being inspected. For example, in selected embodiments, a backbar 42 may include one or more canting mechanisms 48. A canting mechanism 48 may be formed as an integral or monolithic part of a backbar 42. Alternatively, a canting mechanism 48 may be separable from the rest of a backbar 42.

A canting mechanism 48 may form a base for securing a magnet 32, magnet mount 46, or a combination thereof to the rest of the backbar 42 or inspection assembly 12. Accordingly, a canting mechanism 48 may tilt a corresponding magnet 32 or magnet mount 46 toward closer and better (e.g., better aligned) contact with the curved interior surface of the pipeline being inspected.

In selected embodiments, a backbar 42 may include two canting mechanisms. A first canting mechanism 48 may tilt a first magnet 32 one way while a second canting mechanism 48 may tilt a second magnet 32 an opposite way. Accordingly, both magnets 32 and corresponding magnet mounts 46 may be better aligned with the curved pipeline surface most proximate thereto.

A sensor mount 50 in accordance with the present invention may be formed of a flexible material and permit relative motion between a sensor housing 52 and a backbar 42. Constraints such as the magnet mount 46 may be positioned proximate a sensor mount 50 to control or limit certain motion of the sensor mount 50 and sensor housing 52 with respect to the backbar 42. In selected embodiments, a constraint 46 may prevent the sensor housing 52 from contacting or being crushed between a backbar 42 and the wall of the pipeline being inspected. Accordingly, a constraint 46 may provide an additional control over the motion of a sensor housing 52 with respect to a backbar 42.

Inspection assemblies 12 may move with respect to the interior cylinder or main body of an in-line inspection tool 10. For example, inspection assemblies 12 may move in a radial direction 56 with respect to the rest of an in-line inspection tool 10. This freedom of motion may accommodate changes in the pipe being inspected. For example, features such as bends, constrictions, changes in the thickness of the wall of the pipe, circumferential welds, dents, and damaged pipe walls may all affect the interior diameter of a pipeline. Movement of an inspection assembly 12 may permit sensor housings 52 to closely track the interior surface of a pipeline in spite of changes in the interior diameter thereof.

In embodiments utilizing magnetostrictive EMAT inspection, magnets 32 may induce a magnetic flux field in the wall of the pipe being inspected. One or more coils 54 (e.g., meander coils 54) housed within or on a sensor housing 52 may generate, receive, or both generate and receive magnetostrictive stress waves. Such waves may support detection of anomalies within the wall of the pipe being inspected.

Figure 3:
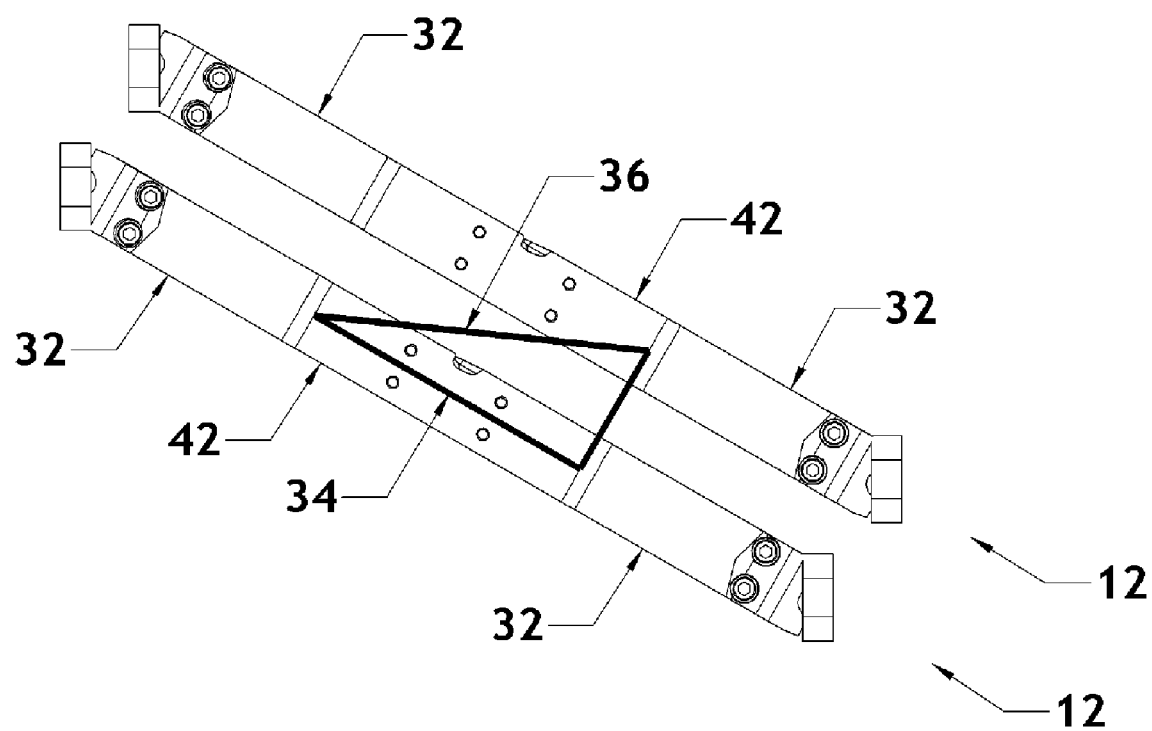
FIG. 3 is a plan view of adjacent inspection assemblies collectively producing an oblique or spiral magnetic field in accordance with the present invention.

Referring to FIG. 3, in certain embodiments, two magnets 32 forming a magnetic dipole pair may be positioned at opposite ends of a backbar 42 so that the distance 34 between poles of the dipole pair is less than the distance 36 between poles of opposite polarity in adjacent inspection assemblies 12. Accordingly, the shortest magnetic flux path in the pipe wall between any poles of opposite polarity may lie parallel to the backbars 42 of the inspection assemblies 12. In such embodiments, the magnetic field may be constrained to the spiral direction of the dipole pair, oblique to both the axial and circumference directions of the pipeline being inspected.

In general, any configuration in which dimension 34 is less than dimension 36 may produce a spiral or oblique magnetic field in accordance with the present invention. In selected embodiments, the placement of adjacent inspection assemblies 12 may be such that the poles of a given polarity (i.e., either North or South) lie in a spiral that is orthogonal to the axis of the inspection assembly 12. In such a configuration, the direction of the spiral comprising the North or the South poles of the magnetic dipoles will be, at all points therealong, orthogonal to the spiral of the magnetic field generated.

In selected embodiments of the configuration discussed above, continuous poles, rather than the discrete poles 32 of FIG. 2, may be used to generate the spiral or oblique magnetic field in accordance with the present invention. Continuous poles may be configured in any suitable manner. For example, in certain embodiments, continuous poles may comprise brush contacts extending from magnets 32 radially outward to the interior surface of the pipeline being inspected.

In such embodiments, the magnets 32 and the brush contacts may be mounted on moveable backbars 42 or on a substantially rigid structure (e.g., cylinder 38) forming part of the frame or backbone of the in-line inspection tool 10. When so configured, the continuous poles will produce polarity that is orthogonal to the line of the poles. When the line of the continuous poles lies in a spiral direction, the desired spiral or oblique magnetic field will be produced in the orthogonal direction, oblique to both the axial and circumferential directions of the pipeline. Such a configuration will always satisfy the required relationship between dimensions 34 and 36 and the dimension 36 will have no practical meaning. A spiral magnetic field produced by continuous poles may be used as the magnetic field for EMAT applications as illustrated herein or for any other compatible defect detection system or technology.

Figure 4:
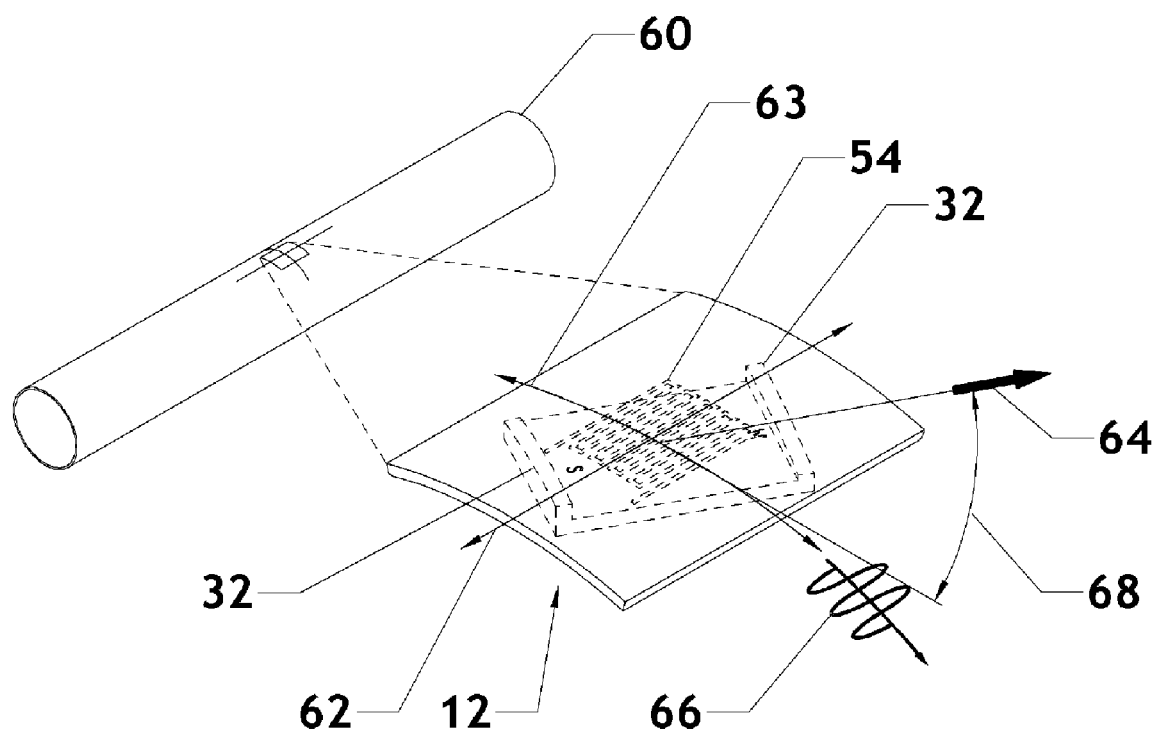
FIG. 4 is a schematic diagram illustrating a magnetostrictive EMAT inspection device positioned to produce a horizontal shear inspection wave guided circumferentially within the wall of the pipe being inspected in accordance with the present invention.

Referring to FIG. 4, a magnetic field 64 may be introduced by the magnets 32 of the inspection assembly 12 into the wall of a pipe segment 60 or pipeline 60 being inspected. The magnets 32 may be permanent magnets or electromagnets. The magnets 32 may be oriented such that the magnetic field 64 is oblique to both the axial direction 62 and circumferential direction 63 defined by the pipe 60. In selected embodiments, the angle 68 between the circumferential direction 63 and the magnetic bias field 64 may have a value of zero to ninety degrees.

In certain embodiments, in addition to one or more magnets 32, an inspection assembly 12 may include a magnetostrictive EMAT. An EMAT may comprise a transmitting coil 54 (e.g., a meander coil 54) oriented with its long axis parallel to the axial direction 62. When the transmitting coil 54 is activated (e.g., by an alternating current pulse), a magnetostrictive force may generate an ultrasonic guided transverse shear wave 66 within the wall of the pipe 60. The wave 66 may be directed in the circumferential direction 63, perpendicular to the axis of the coil 54. In certain embodiments, to maximize the strength of this wave 66, the angle 68 between the circumferential direction 63 and the magnetic bias field 64 may have a value of ten to sixty degrees.

Figure 5:
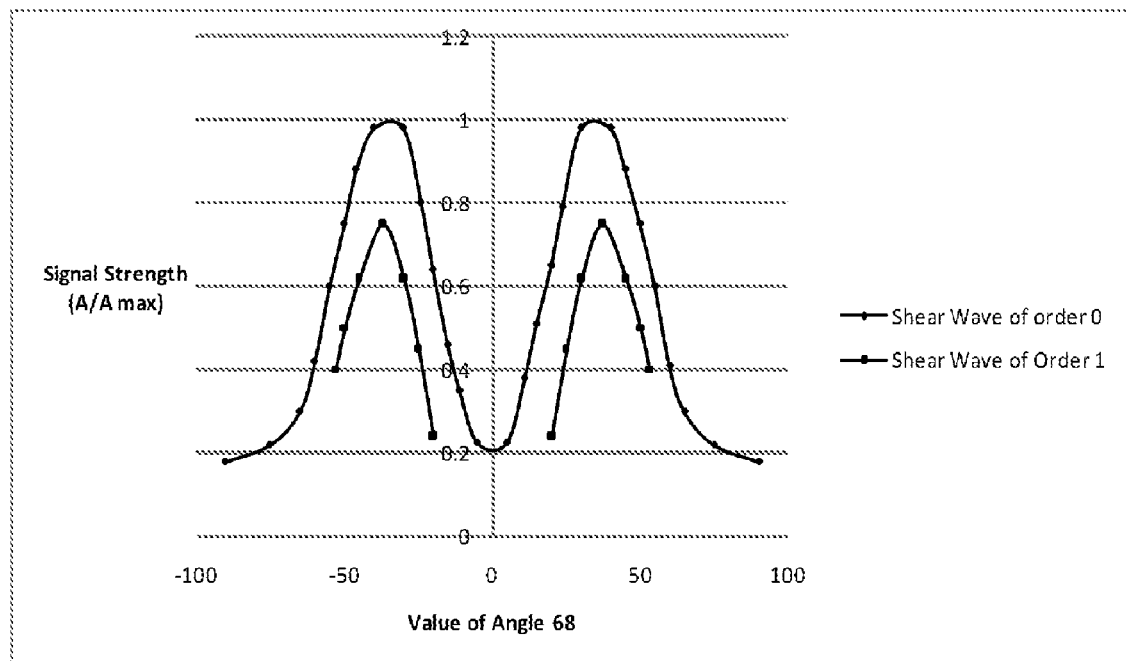
FIG. 5 is a graph illustrating the relationship between a magnetic field orientation and signal amplitude.

Referring to FIG. 5, the strength of a wave 66 may vary with the angle 68 between the circumferential direction 63 and the magnetic bias field 64. When the angle 68 is ninety degrees, the bias field 64 and the long axis of the meander coil 54 are both parallel to the axial direction 62 of a pipe 60. In such a configuration, only a circumferential transverse shear wave 66 is transmitted. However, the strength of the wave 66 is not at its maximum.

As illustrated on the graph of FIG. 5, the amplitude of the circumferential transverse shear wave 66 may be increased by orienting the magnetic field 64 relative to the coil 52 so that the angle 68 has a value of about ten to about sixty degrees. In selected embodiments, the amplitude of the circumferential transverse shear wave 66 may be further increased by orienting the magnetic field 64 relative to the coil 54 so that the angle 68 has a value of about twenty to about fifty degrees. In still other embodiments, the amplitude of the circumferential transverse shear wave 66 may be further increased by orienting the magnetic field 64 relative to the coil 52 so that the angle 68 has a value of about thirty to about forty degrees.

When the magnitude of a circumferential horizontal shear wave 66 is increased via the angle 68 between the circumferential direction 63 and the magnetic field 64, waves other than the horizontal shear wave 66 may be emitted. These other waves may themselves be used for pipeline inspection. Alternatively, they may be removed by frequency filtering, time gating, or other digital signal processing consistent with the nature of the initiating pulse.

Figure 6:
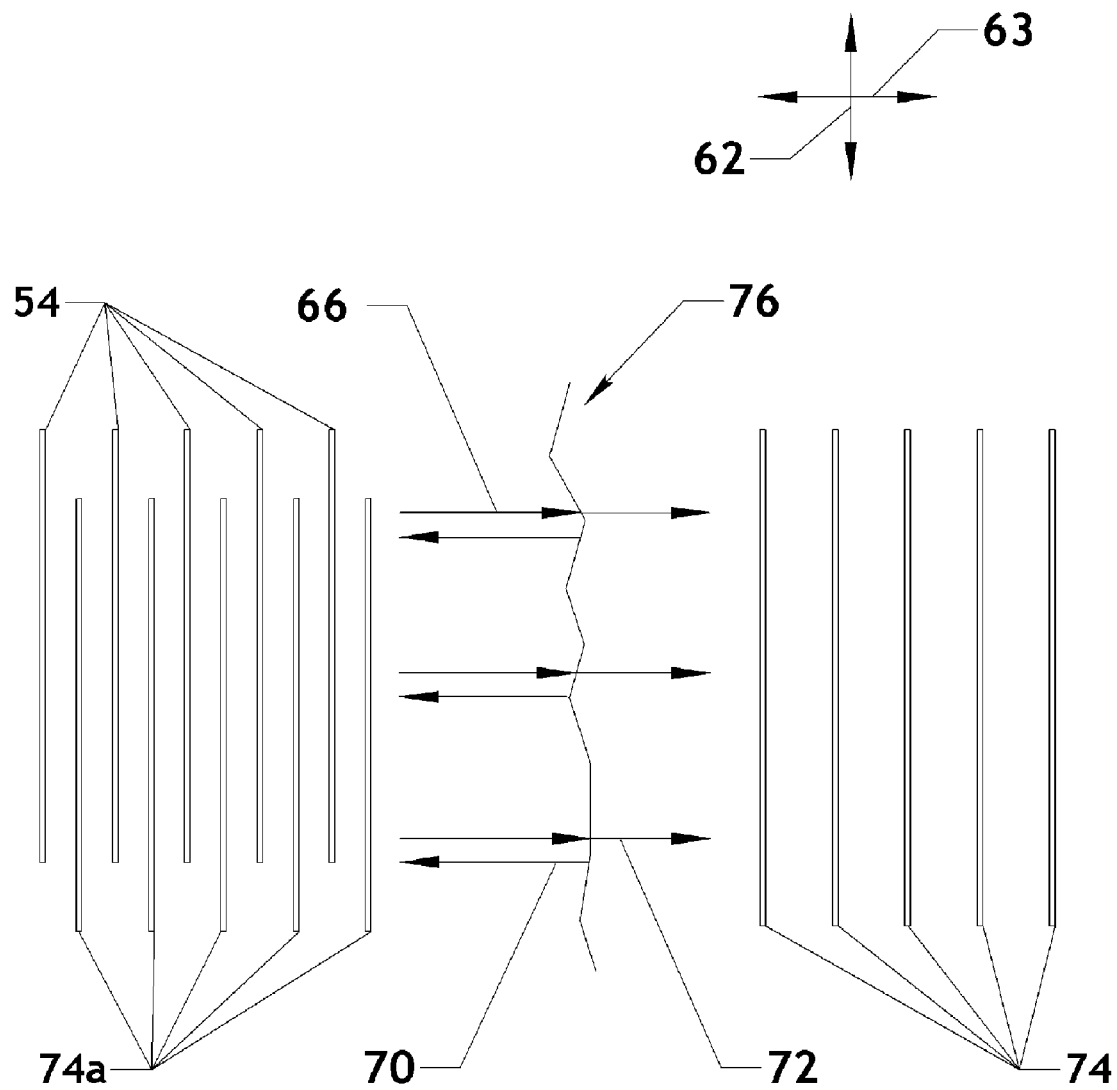
FIG. 6 is a schematic diagram illustrating selected embodiments of elements of coils of an EMAT in-line inspection tool showing their positions relative to one another and to signals generated and/or received thereby in accordance with the present invention.

Referring to FIG. 6, once produced, a horizontal shear wave 66 may be guided by the surfaces of the pipe wall to travel around the circumference of the pipe 60. In so doing, the wave 66 may encounter an obstruction such as a defect 76 in the pipe wall. A defect 76 may produce a reflected pulse 70 that can be received at or near the location of the transmitting coil 54 in a pulse-echo mode. A defect 76 may also alter the portion 72 of the wave 66 that passes the defect 76.

The altered wave 72 may be received by a receiving coil 74 located past the defect 76 in a pitch-catch mode. This receiving coil 74 may be located anywhere up to three hundred sixty degrees around the pipe 60 in the circumferential direction 63 (e.g., to the point where it would overlay the transmitting coil 54). In selected embodiments, at three hundred sixty degrees, the receiving coil 74 may comprise the transmitting coil 54 in a non-transmitting mode. The receiving coil 74 may even be slightly more than three hundred sixty degrees around the circumference of the pipe 60. Accordingly, the entire circumference of the pipe 60 may be inspected by one or more such devices 54, 74.

Embodiments in accordance with the present invention may include any suitable combination of transmitter and receiver including, without limitation, a transmitting coil 54 used as both a transmitter and receiver in a pulse-echo mode; a transmitting coil 54 with a separate, comparable receiving coil 74a placed within the magnetic field 64 or in a similar magnetic field slightly ahead of the transmitting coil 54 in a pulse-echo mode; a transmitting coil 54 with a comparable receiving coil 74 in a comparable magnetic field placed beyond the location of potential axially oriented defects 76 as a receiver in a pitch-catch mode; a transmitting coil 54 used as a transmitter and receiver in a pitch-catch mode for guided waves traveling three hundred sixty degrees completely around the circumference of the pipe; or a transmitting coil 54 with a separate comparable receiving coil 74a placed within the magnetic field 64 or in a similar magnetic field slightly removed from the transmitting coil 54 in a pitch-catch mode for guided waves 66 traveling just under or just over three hundred sixty degrees around the circumference of the pipe 66.

Figure 7:
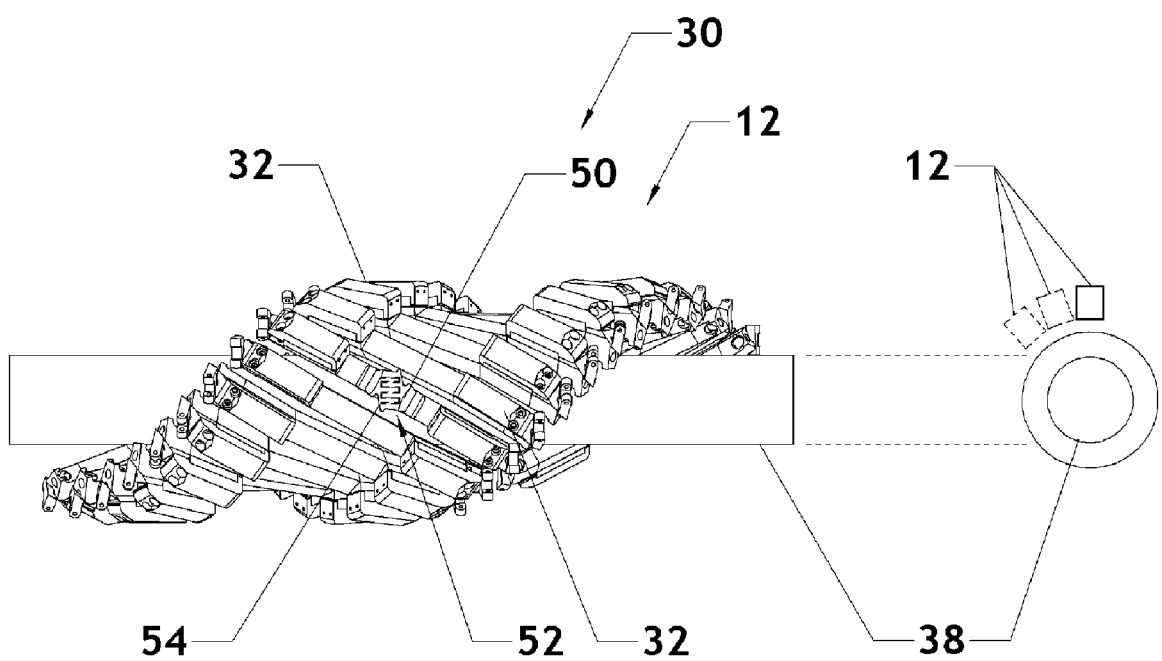
FIG. 7 is an elevation view of one embodiment of a series of North-South dipole pairs positioned to produce a spiral magnetic field oblique to both the axial and circumferential directions of the pipeline in accordance with the present invention.

Referring to FIG. 7, in selected embodiments in accordance with the present invention, multiple inspection assemblies 12 may be placed side-by-side in a single continuous spiral. Positioned in this way, the magnets 32 of the various assemblies 12 may strengthen the magnitude of the overall magnetic field. They may do this by limiting lateral spread of the magnetic field orthogonal to the North-South axis thereof.

In certain embodiments, multiple meander coils 54 may be placed in the several magnetic fields 64 to increase inspection coverage of the pipe wall via the multiple shear waves 66 they produce. For example, coils 54 may be placed in every North-South magnetic dipole (e.g., in every inspection assembly 12). Alternatively, coils 54 may be placed in alternating dipoles or in any succession of dipoles that may be selected. Coils 54 may then be used as both transmitters and receivers for a full three hundred sixty degree examination of a section of the pipeline 60. Multiple sections and periodic pulsing of the coils 54 at each section may ensure thorough examination of the pipe wall.

Figure 8:
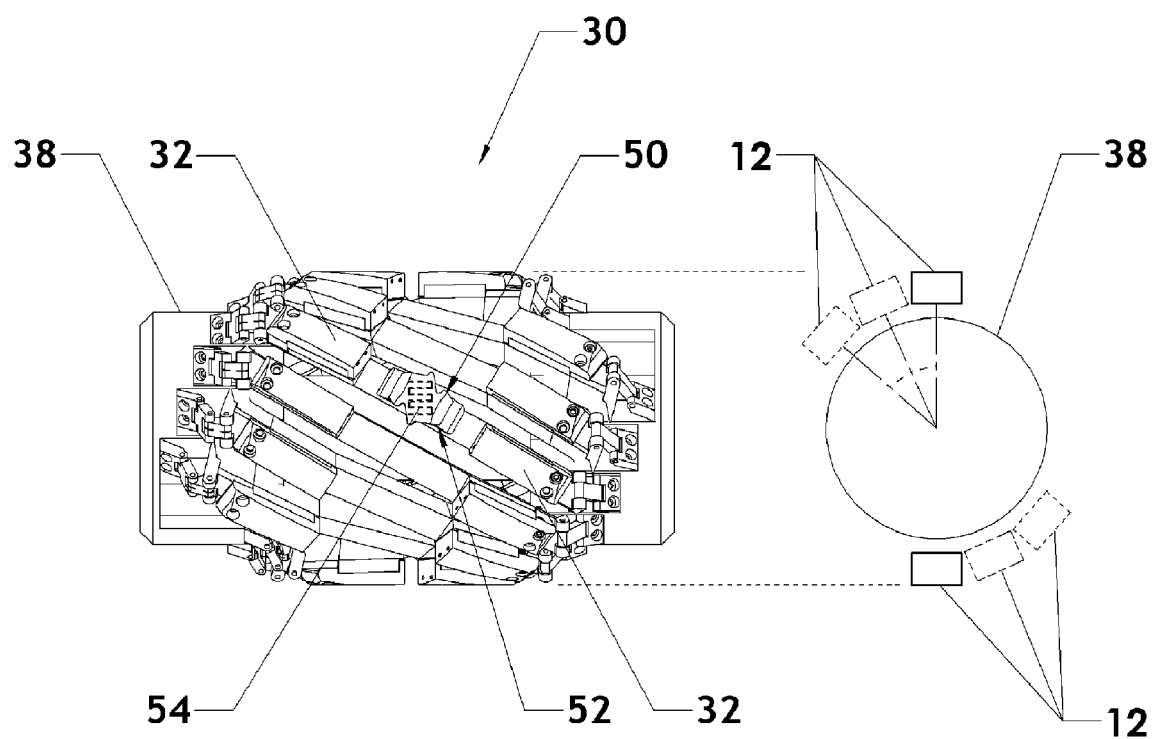
FIG. 8 is an elevation view of an alternative embodiment of a series of North-South dipole pairs positioned to produce a spiral magnetic field oblique to both the axial and circumferential directions of the pipeline in accordance with the present invention.

Referring to FIG. 8, in selected embodiments in accordance with the present invention, multiple inspection assemblies 12 may be placed side-by-side in two continuous spirals spaced one hundred eighty degrees apart around the circumference of an in-line inspection tool 10 or section thereof. In this configuration, one meander coil 54 may be placed as a transmitter in a North-South dipole field (e.g., in a first inspection assembly 12), while another meander coil 54 may be placed as a receiver in the corresponding, opposite North-South dipole field (e.g., in a second inspection assembly 12) spaced one hundred eighty degrees therefrom. Other transmitter and receiver pairs may be placed in this or some other manner to increase inspection coverage.

Figure 9:
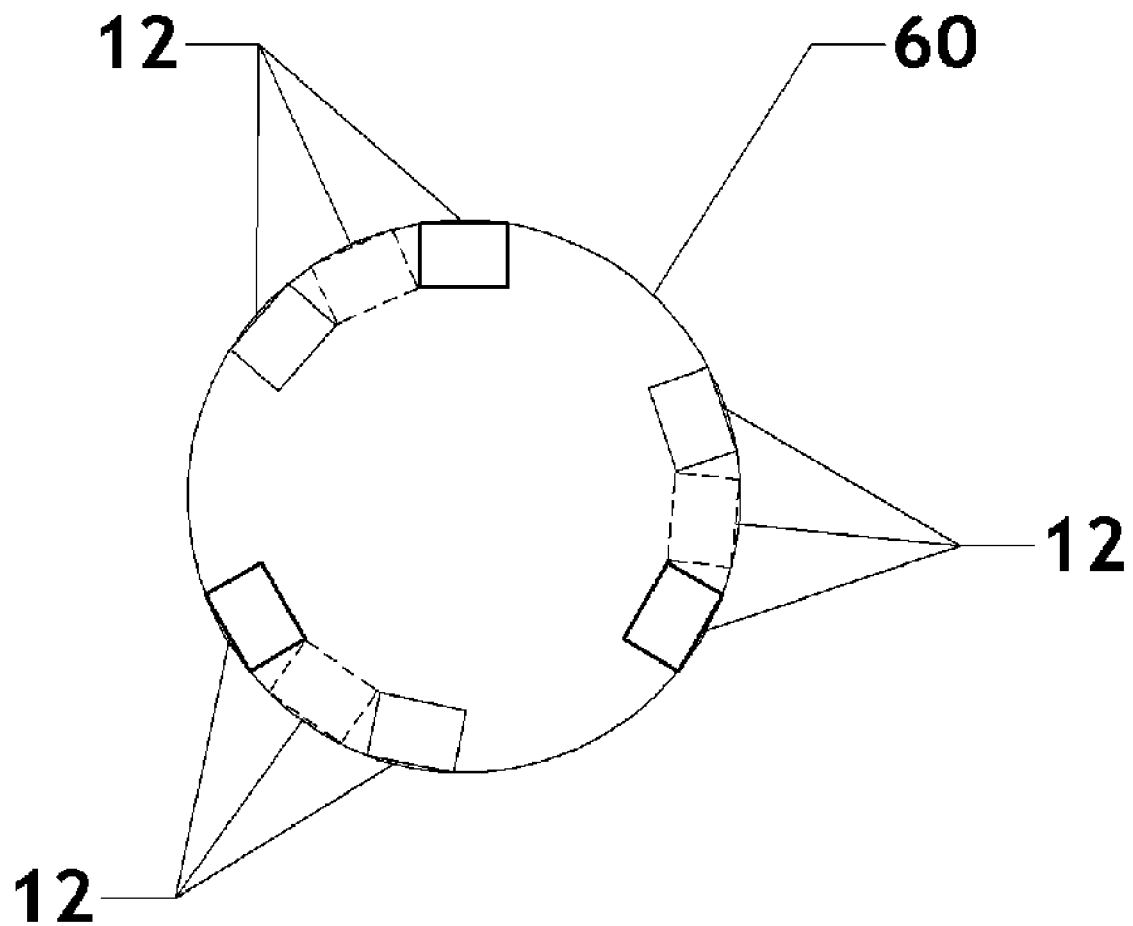
FIG. 9 is a schematic front view of another alternative embodiment of a series of North-South dipole pairs positioned to produce a spiral magnetic field oblique to both the axial and circumferential directions of the pipeline in accordance with the present invention.

Referring to FIG. 9, in still other embodiments in accordance with the present invention, multiple inspection assemblies 12 may be placed side-by-side in three continuous spirals spaced one hundred twenty degrees apart around the circumference of an in-line inspection tool 10 or section thereof. In this configuration, meander coils 54 may be placed (e.g., within inspection assemblies 12) as desired or necessary.

Still other configurations may comprise more coaxial spirals to reduce the circumferential spacing between transmitter and receiver coils. Each North-South dipole magnetic field may have an axial and a circumferential component that may be used separately or together for the inspection of pipeline using inspection technologies other than EMAT.

Figure 10:
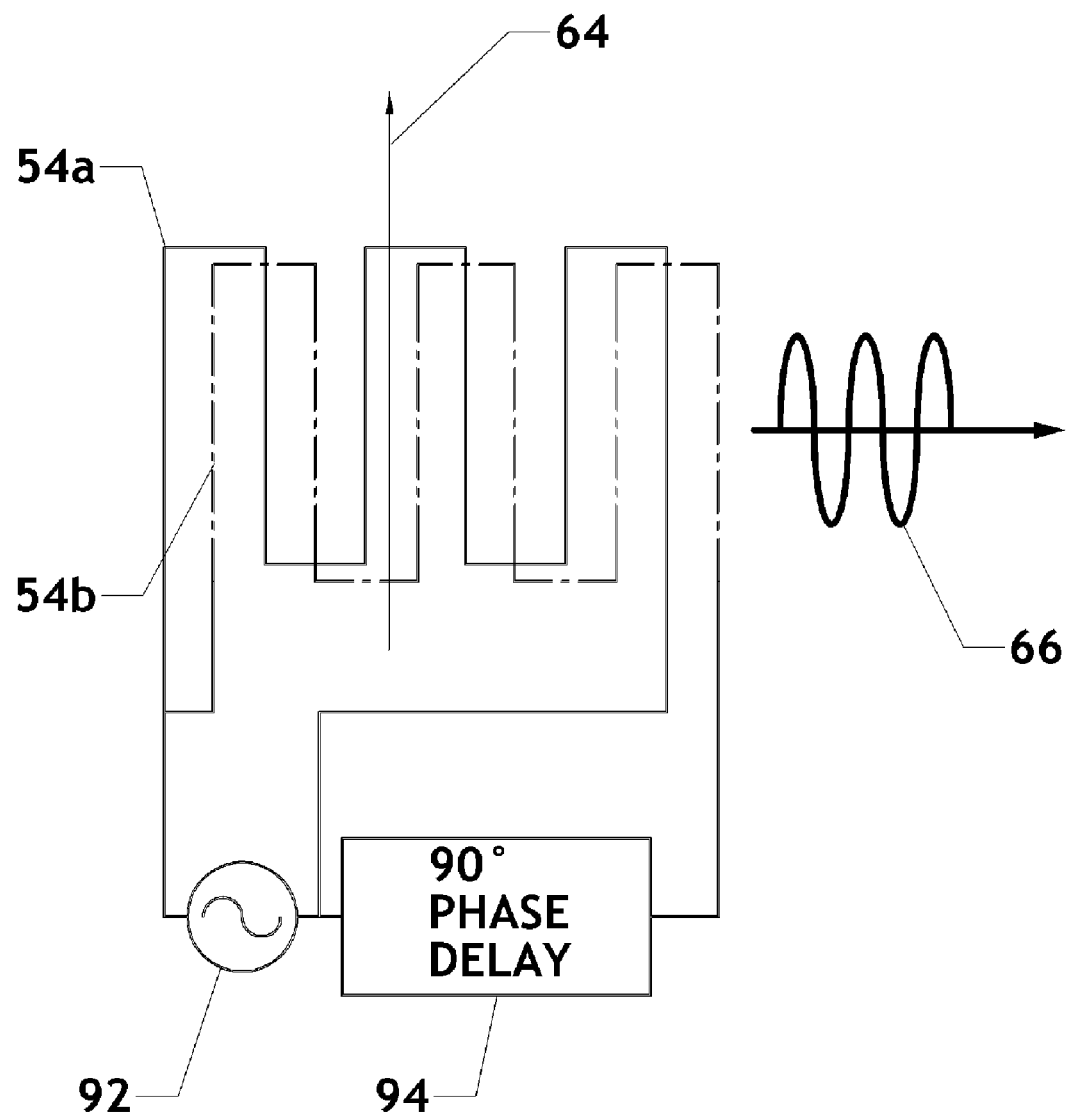
FIG. 10 is a schematic diagram illustrating a meander coil pair propagating a shear pulse in only one direction.

Referring to FIG. 10, an EMAT in accordance with the present invention may generate both a forward moving wave 66 and a backward moving wave separated one hundred eighty degrees from one another. In selected embodiments, a backward traveling wave may be eliminated. For example, an EMAT may comprise two meander coils 54a, 54b. One meander coil 54b may be placed forward of the other meander coil 54a in the direction of the transmitted transverse shear wave 66 by one-half the distance between coil elements. The forward meander coil 54b may be activated by an alternating current pulse 92 identical to the pulse activating the other meander coil 54a, but phase delayed 94 by ninety degrees. The magnetostrictive forces that create transverse shear waves 66 from the two meander coils 54a, 54b may add to each other in one direction and cancel each other in the opposite direction. Accordingly, they may produce a transverse shear wave 66 in one direction only.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A system comprising:
    a portion of pipe comprising a pipe wall forming a cylindrical tube defining a circumferential direction and an axial direction; and
    an in-line inspection tool positioned within the portion of pipe and comprising
        a frame extending in the axial direction,
        a plurality of armatures, each armature thereof being independently suspended from the frame,
        the plurality of armatures, each armature thereof comprising two magnets spaced apart a first distance to form a magnetic dipole pair,
        the plurality of armatures connected to the frame with the first distance being the shortest distance between any poles of opposite polarity contained within the plurality of armatures, and
        the magnetic dipole pair of each armature of the plurality of armatures generating a magnetic field oriented obliquely with respect to the circumferential and axial directions.

2. The system of claim 1, further comprising a first transmitter connected to a first armature of the plurality of armatures at a location between the two magnets of the first armature.

3. The system of claim 2, wherein the first transmitter cooperates with the two magnets of the first armature to form an electromagnetic acoustic transducer.

4. The system of claim 3, wherein the electromagnetic acoustic transducer generates within the pipe wall a transverse shear wave traveling in the circumferential direction.

5. The system of claim 4, wherein the in-line inspection tool further comprises at least one receiver connected to the frame.

6. The system of claim 5, wherein the at least one receiver comprises the first transmitter in a non-transmitting mode.

7. The system of claim 5, wherein the at least one receiver comprises hardware, distinct from the first transmitter.

8. The system of claim 5, wherein the at least one receiver receives from the pipe wall the transverse shear wave.

9. The system of claim 8, wherein the first transmitter resides in at least one of the magnetic field generated by the first armature and a component of the magnetic field generated by the first armature that is aligned with the axial direction.

10. The system of claim 2, further comprising a second transmitter connected to a second armature of the plurality of armatures at a location between the two magnets of the second armature.

11. The system of claim 2, wherein the first transmitter comprises a plurality of electric conductors connected in series and carrying one of pulsed direct and alternating current in the axial direction.

12. The system of claim 11, wherein the magnetic field generated by the first armature is oriented with respect to the circumferential direction at an angle between ten and sixty degrees.

13. The system of claim 12, wherein the magnetic field generated by the first armature is oriented with respect to the circumferential direction at an angle between twenty and fifty degrees.

14. The system of claim 2, further comprising at least one receiver, the at least one receiver comprising the first transmitter in a non-transmitting mode.

15. The system of claim 1, wherein the two magnets of each armature of the plurality of armatures each comprise a permanent magnet.

16. The system of claim 1, wherein the two magnets of each armature of the plurality of armatures each comprise an electromagnet activated by one of constant and pulsed current.

17. A system comprising:
    a portion of pipe comprising a pipe wall forming a cylindrical tube defining a circumferential direction and an axial direction; and
    an in-line inspection tool positioned within the portion of pipe and comprising
        a frame extending in the axial direction,
        a plurality of armatures, each being independently suspended from the frame and comprising a first end and a second end, opposite the first end,
        a plurality of first magnets, each connected to the first end of a different armature of the plurality of armatures to form a first pole,
        a plurality of second magnets, each connected to the second end of a different armature of the plurality of armatures to form a second, opposite pole,
        the plurality of armatures, wherein a distance between the first and second poles corresponding to a first armature thereof is less than a distance between the first pole corresponding to the first armature and the second pole corresponding to an adjacent armature of the plurality of armatures, and
        the plurality of armatures, wherein the first and second magnets corresponding to each armature thereof generate a magnetic field orientated obliquely with respect to the circumferential and axial directions.

18. A system comprising:
    a portion of pipe comprising a pipe wall forming a cylindrical tube defining a circumferential direction and an axial direction; and
    an in-line inspection tool positioned within the portion of pipe and comprising
        a frame extending in the axial direction,
        the frame comprising a plurality of rigid sections connected together in series by one or more flexible couplers,
        a plurality of armatures connected to a rigid section of the plurality of rigid sections,
        the plurality of armatures, each armature thereof comprising two magnets spaced apart a first distance to form a magnetic dipole pair,
        the plurality of armatures connected to the frame with the first distance being the shortest distance between any poles of opposite polarity contained within the plurality of armatures, and
        the magnetic dipole pair of each armature of the plurality of armatures generating a magnetic field oriented obliquely with respect to the circumferential and axial directions.

19. The system of claim 18, wherein the plurality of armatures are distributed spirally with respect to the rigid section.

20. The system of claim 18, wherein each armature of the plurality of armatures is independently suspended form the rigid section.

* * * * *